United States Patent
Moon et al.

(10) Patent No.: US 8,230,723 B2
(45) Date of Patent: Jul. 31, 2012

(54) HIGH PRESSURE HIGH TEMPERATURE VISCOMETER

(75) Inventors: John Jeffery Moon, Tulsa, OK (US); Brian Roland Ainley, Broken Arrow, OK (US)

(73) Assignee: Chandler Instruments Company, LLC, Broken Arrow, OK (US)

( * ) Notice: Subject to any disclaimer, the term of this patent is extended or adjusted under 35 U.S.C. 154(b) by 401 days.

(21) Appl. No.: 12/234,358

(22) Filed: Sep. 19, 2008

(65) Prior Publication Data

US 2010/0071442 A1    Mar. 25, 2010

(51) Int. Cl.
  *G01N 11/14* (2006.01)
(52) U.S. Cl. ............ 73/54.28; 73/54.31; 73/54.32; 73/54.33; 73/54.34
(58) Field of Classification Search ............ 73/54.32
  See application file for complete search history.

(56) References Cited

U.S. PATENT DOCUMENTS

| | | |
|---|---|---|
| 2,713,790 A | 7/1955 | Barber et al. |
| 3,435,666 A | 4/1969 | Fann |
| 4,157,029 A | 6/1979 | Leca et al. |
| 4,426,878 A | 1/1984 | Price et al. |
| 4,466,276 A | 8/1984 | Ruyak et al. |
| 4,499,753 A | 2/1985 | Carr |
| 4,524,611 A | 6/1985 | Richon et al. |
| 4,539,837 A | 9/1985 | Barnaby |
| 4,622,846 A | 11/1986 | Moon, Jr. et al. |
| 4,630,468 A | 12/1986 | Sweet |
| 4,747,720 A * | 5/1988 | Bellehumeur et al. ........ 401/205 |
| 4,878,378 A * | 11/1989 | Harada ........ 73/54.35 |
| 4,916,678 A | 4/1990 | Johnson et al. |
| 5,526,680 A | 6/1996 | McLaughlin |
| 5,535,619 A | 7/1996 | Brookfield |
| 6,575,019 B1 | 6/2003 | Larson |
| 7,287,416 B1 | 10/2007 | Bi |
| 7,441,442 B2 * | 10/2008 | Morgan ........ 73/54.43 |

* cited by examiner

*Primary Examiner* — Hezron E Williams
*Assistant Examiner* — Paul West
(74) *Attorney, Agent, or Firm* — Fellers, Snider, Blankenship, Bailey & Tippens, P.C.

(57) ABSTRACT

A couette viscometer used to determine the rheological properties of Newtonian or non-Newtonian solid-laden or non-solid-laden fluids used as completion or treatment fluids in oil and/or gas wells. The instrument is capable of measuring the properties of a heated, e.g., 600° F./316° C., and pressurized sample, e.g., 30,000 psig/207 MPa, at a variety of temperatures, pressures, and shear rates. The pressure vessel is mounted in the chassis of the instrument and the vessel plug containing the viscometer components and sample may be removed as an assembly. This arrangement reduces the mass of the plug assembly, eliminating the need to transport the pressure vessel and assists in separating the sample from the pressurizing fluid. Ultimately, this arrangement improves the usability, convenience and maintenance associated with operating the instrument.

11 Claims, 7 Drawing Sheets

HIGH PRESSURE HIGH TEMPERATURE VISCOMETER

FIELD OF THE INVENTION

The present invention relates generally to a couette viscometer for measuring samples at high pressure and high temperature conditions. More particularly, the viscometer of the invention is designed to improve usability, convenience and maintenance associated with operating the instrument.

BACKGROUND OF THE INVENTION

Rotational viscometers measure fluid shear stress created by known shear rates. Viscosity is defined as the ratio of shear stress to shear rate, commonly expressed in units of Poise. The shear stress is proportional to the torque induced on a cylindrical object immersed in a fluid surrounded by a concentric cylindrical surface that is rotated at known speeds. The shear rate is a function of the rotational speed and the geometry.

One type of rotational viscometer is a couette viscometer. In a couette viscometer, liquid whose viscosity is to be measured fills a space between two vertical coaxial cylinders. The inner cylinder is suspended while the outer cylinder is rotated at a constant rate using a computer controlled stepper motor. The resulting torque on the inner cylinder is accurately measured to determine shear stress.

Couette viscometers may be used to determine Theological properties of Newtonian or non-Newtonian solid-laden or non-solid-laden fluids used as completion or treatment fluids in oil and/or gas wells. It is desirable to test such fluids at high temperatures and high pressures.

In a typical instrument a pressure vessel capable of withstanding high temperatures and pressures is provided to contain the cup and bob of the viscometer. After testing is conducted, the pressure vessel must be removed from the instrument to change the sample fluid and to clean the components.

To withstand high temperatures and pressures, the pressure vessel is constructed of heavy materials and, is therefore, difficult to remove and inconvenient to handle and manipulate. It is therefore desirable to provide a viscometer for measuring high pressure and high temperature samples that has a construction to facilitate ease of operation and cleaning.

SUMMARY OF THE INVENTION

In the viscometer of the invention, a sample is contained by a pressure vessel and plug assembly. Due to the containment, the sample may be heated and pressurized as a part of simulating conditions in an oil or gas well. Once the conditions are stable, the sample viscosity is determined through measurement of shear stresses at known shear rates.

The viscometer of the invention is preferably a couette type and may be used to determine the rheological properties of Newtonian or non-Newtonian solid-laden or non-solid-laden fluids used as completion or treatment fluids in oil and gas wells. The instrument is capable of measuring the properties of a heated, e.g., 600° F., and pressurized sample, e.g., 30,000 psig, at a variety of temperatures, pressures, and shear rates.

The sample is contained within in a sample cup located inside the pressure vessel. The sample cup serves to separate the sample fluid from pressurizing fluid and facilitates removal of the sample when the plug assembly is removed.

The sample cup contains a magnet assembly, e.g., a SmCo magnet assembly, a rotor assembly, a thermowell and related bearings and bushing. A bob assembly is supported by a jewel bearing pivot. The magnet assembly couples to an opposing magnet assembly that is located outside of the pressure vessel, e.g., a second SmCo magnet assembly. By rotating the outer magnet assembly at known speeds using a stepper motor, motion of the inner magnet assembly and rotor is induced. The thermowell provides a means to accurately measure the sample temperature on the centerline of the assembly within the confines of the bob assembly.

The sample cup is pressure balanced using high pressure ports that connect to internal and external volumes. Therefore, the sample cup does not resist the pressure and may be constructed with a low mass. The external surface of the sample cup is knurled to improve usability and to improve heat transfer.

The rotor assembly includes external helical flutes that are used to induce circulation of the sample as the rotor assembly is rotated. The circulation path includes the annular volume outside of the rotor assembly, a baffle, an annular volume outside of the bob assembly, ports located in the conical top of the bob assembly, and a volume surrounding the magnet assembly. The baffle above the bob assembly is used to eliminate or reduce the angular momentum of the sample induced by the helical flutes.

Torque, from which shear stress is calculated, is determined by sensing the angular displacement of a spring, e.g., a linear BeCu spring, attached to the bob assembly confined within the sample cup and pressure vessel. The angular displacement of the spring is measured using a high resolution optical encoder that is magnetically coupled to the spring using a magnet assembly, e.g., made up of SmCo magnets. Through appropriate calibration of the spring, angular displacement is related to torque and shear stress. To enhance the sensitivity of the torque measurement through reduction of frictional effects, the optical codewheel within the encoder assembly is supported by sapphire jewel bearings.

Calibration of the instrument is accomplished using known viscosity oil that is loaded into the sample cup and evaluated at pre-determined shear rates. Since the viscosity of the calibration oil and shear rates are known, along with the bob and rotor dimensions, the associated shear stress and torque is determined at each shear rate. The resulting BeCu spring displacement at each shear rate is measured and scaled to indicate shear stress. Using this method and suitable computer software, automatic instrument calibration may be achieved once the calibration oil is loaded into the instrument.

After testing, the plug assembly may be removed from the pressure vessel after releasing the pressure and cooling the sample. Once the encoder assembly and high pressure tube connection components are removed, the plug assembly is rotated to disengage the threads. The high pressure seal components, e.g., an elastomeric and a metallic seal, are removed with the plug assembly. Once removed, the plug assembly may be transported to a plug support bracket. The plug support bracket is provided to support the assembly during removal of the sample cup assembly and sample. Once the sample is removed, further disassembly of the plug may take place as a normal part of instrument clean-up and maintenance operations.

Since the sample cup is pressure balanced, the sample cup and viscometer components may be constructed of a reduced mass. The pressure vessel remains mounted in the instrument chassis. The sample cup containing the viscometer components and sample is removed as an assembly. This arrangement eliminates a need to transport the pressure vessel and assists in separating the sample from the pressurizing fluid.

Therefore, the viscometer of the invention provides improved usability, convenience and ease of maintenance.

DETAILED DESCRIPTION OF THE PREFERRED EMBODIMENTS

Figure 1:
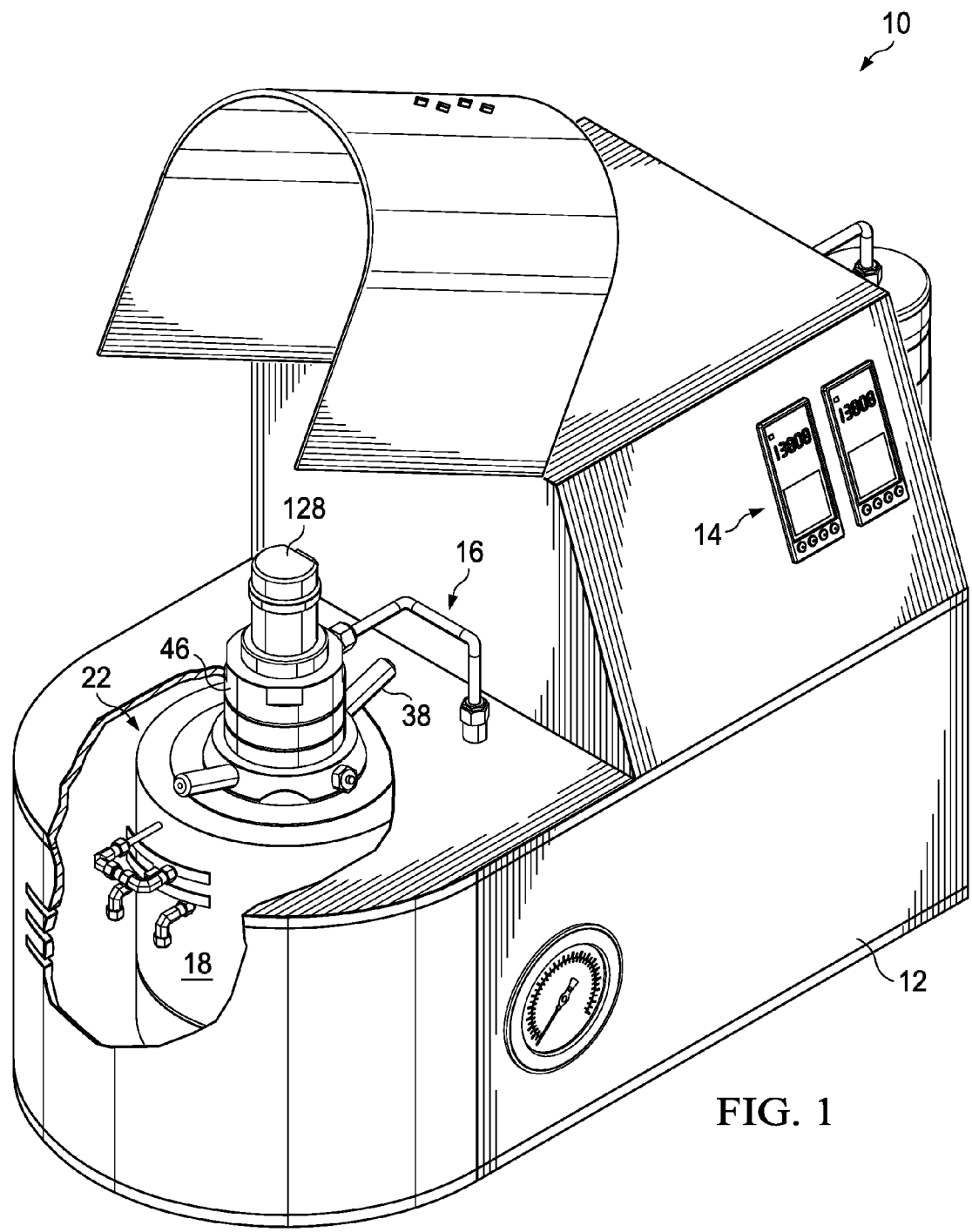
FIG. 1 provides an illustration of the high pressure, high temperature viscometer.
Figure 2:
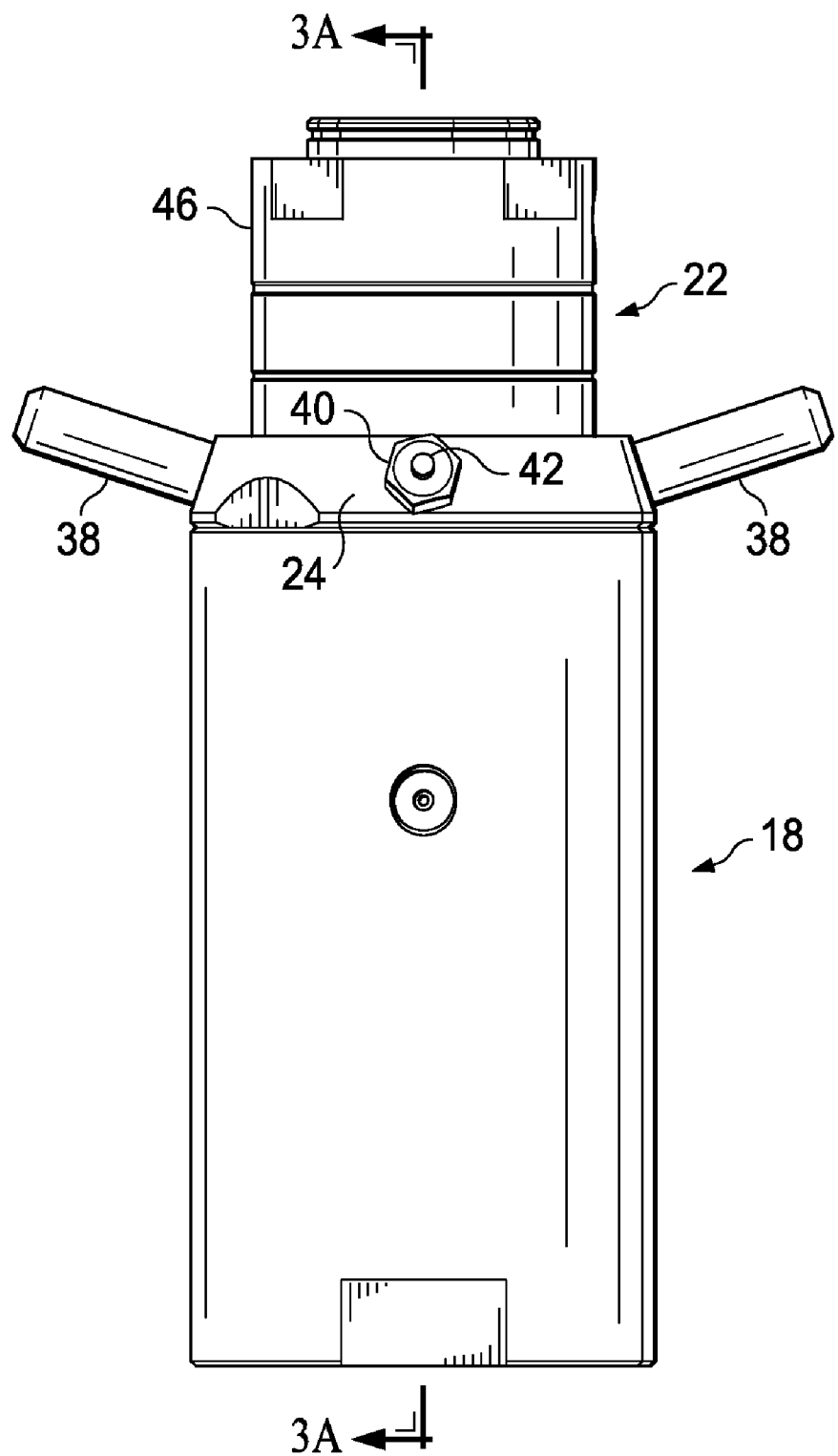
FIG. 2 provides a side view of the plug and vessel assembly.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Referring now to FIGS. 1-7, shown is viscometer unit 10 (FIG. 1) for measuring high temperature and high pressure samples. Viscometer unit 10 includes case enclosed chassis 12. The case houses electronics 14 and hydraulic and pneumatic components 16. Viscometer unit 10 includes a chassis mounted pressure vessel 18 (FIGS. 1-7) that defines receptacle 20 (FIGS. 3A, 3B). Plug assembly 22 is received within receptacle 20 of pressure vessel 18. Plug assembly 22 includes plug top 24 having upper threads 26 and lower threads 28 (FIG. 3A). Plug top 24 defines central orifice 30 (FIGS. 3A, 6) and sample filling passageway 32 (FIGS. 3A, 3B) that communicates with an outer port 34. Sample filling passageway 32 communicates with receptacle 20 of pressure vessel 18 proximate second end 36 to deliver sample fluid 33. Sample fluid 33 may be placed in sample cup 68 prior to assembly. The sample filling passageway 32 is used to inject additional sample thereby displacing sample fluid 33 into the annular volume above baffle 64.

In a preferred embodiment, a plurality of handle members 38 protrude from plug top 24. High pressure gland 40 (FIGS. 2, 3A, 4, 5) is threadably received in plug top 24 at first end 34 of sample filling passageway 32. A plug 42 is retained in port 34 of sample filling passageway 32 and is retained by high pressure gland 40.

Figure 5:
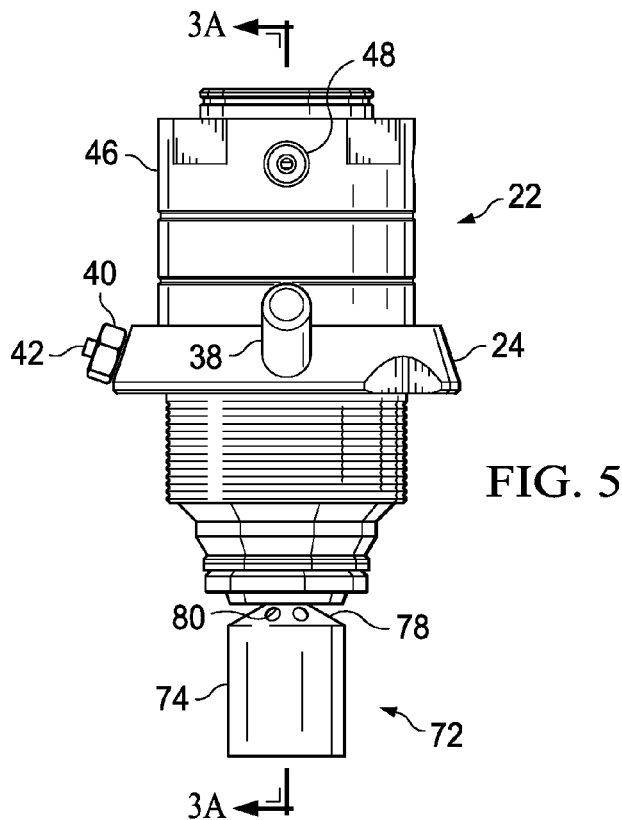
FIG. 5 provides a plan view of the plug assembly with the sample cup removed.
Figure 6:
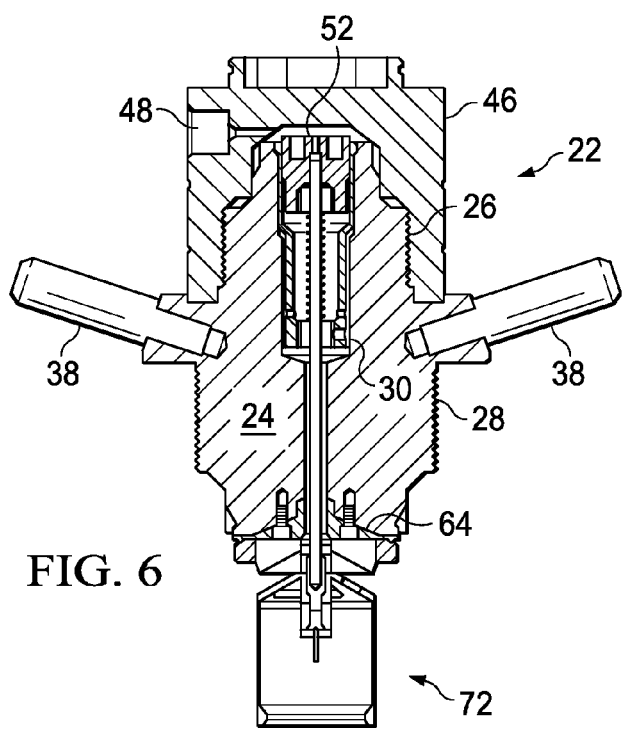
FIG. 6 provides a cross-sectional view of the plug assembly as shown in FIG. 5.

Cap 46 is threadably received on upper threads 26 of plug top 24. Cap 46 defines pressure port 48 (FIGS. 5, 6). Pressure port 48 communicates with an exterior of cap 46 and also communicates with central orifice 30 of plug top 24. Pressure port 48 is adapted to receive a pressure fluid 49. Alignment ring 50 (FIGS. 3A, 4) surrounds plug top 24. Alignment ring 50 is used to assist with orientation of port 48 in cap 46.

Figure 4:
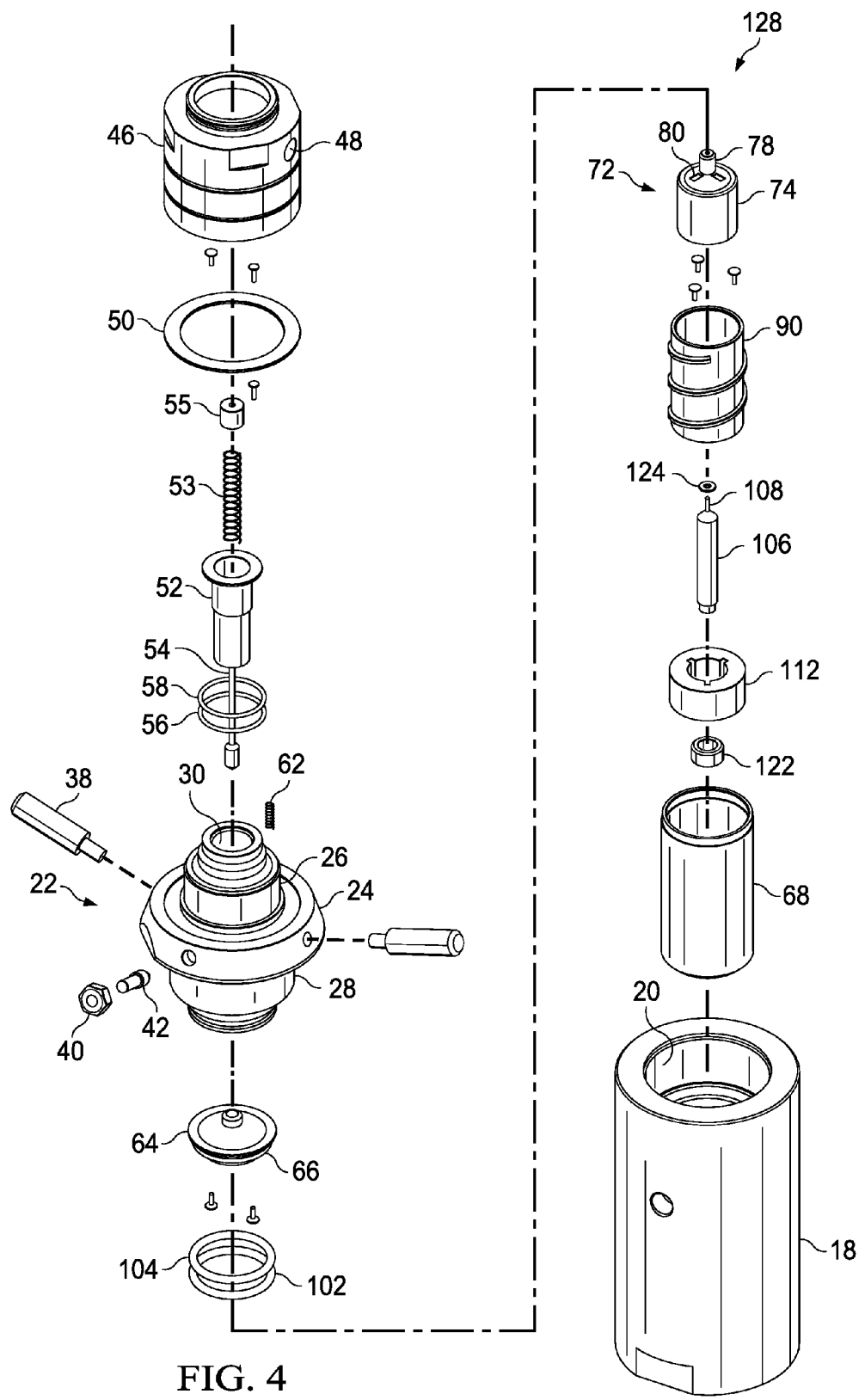
FIG. 4 provides an exploded view of the plug and vessel assembly.

Referring now primarily to FIG. 4, module assembly 52 has shaft 54, spring 53, and magnet 55 that extend downwardly into central orifice 30 of plug top 24. Spring magnet 55 magnetically couples with encoder assembly 128. High pressure o-ring 56 surrounds plug 24. A metal backup ring 58 surrounds plug 24 beneath high pressure seal cap 46. A cap alignment plunger spring 62 for aligning cap 46 surrounds plug 24. Baffle assembly 64 is affixed to a lower end of plug top 24. Baffle assembly 64 is provided with lower threads 66.

Sample cup 68 is threadably received on lower threads 66 of baffle assembly 64. Sample cup 68 defines threaded orifice 70 (FIG. 3A) on a bottom surface thereof. Sample cup 68 is provided for receiving a sample of fluid. Sample cup 68 has a knurled exterior to provide a gripping surface to facilitate ease of unscrewing sample cup 68 from baffle assembly 64 and to improve heat transfer.

Figure 3A:
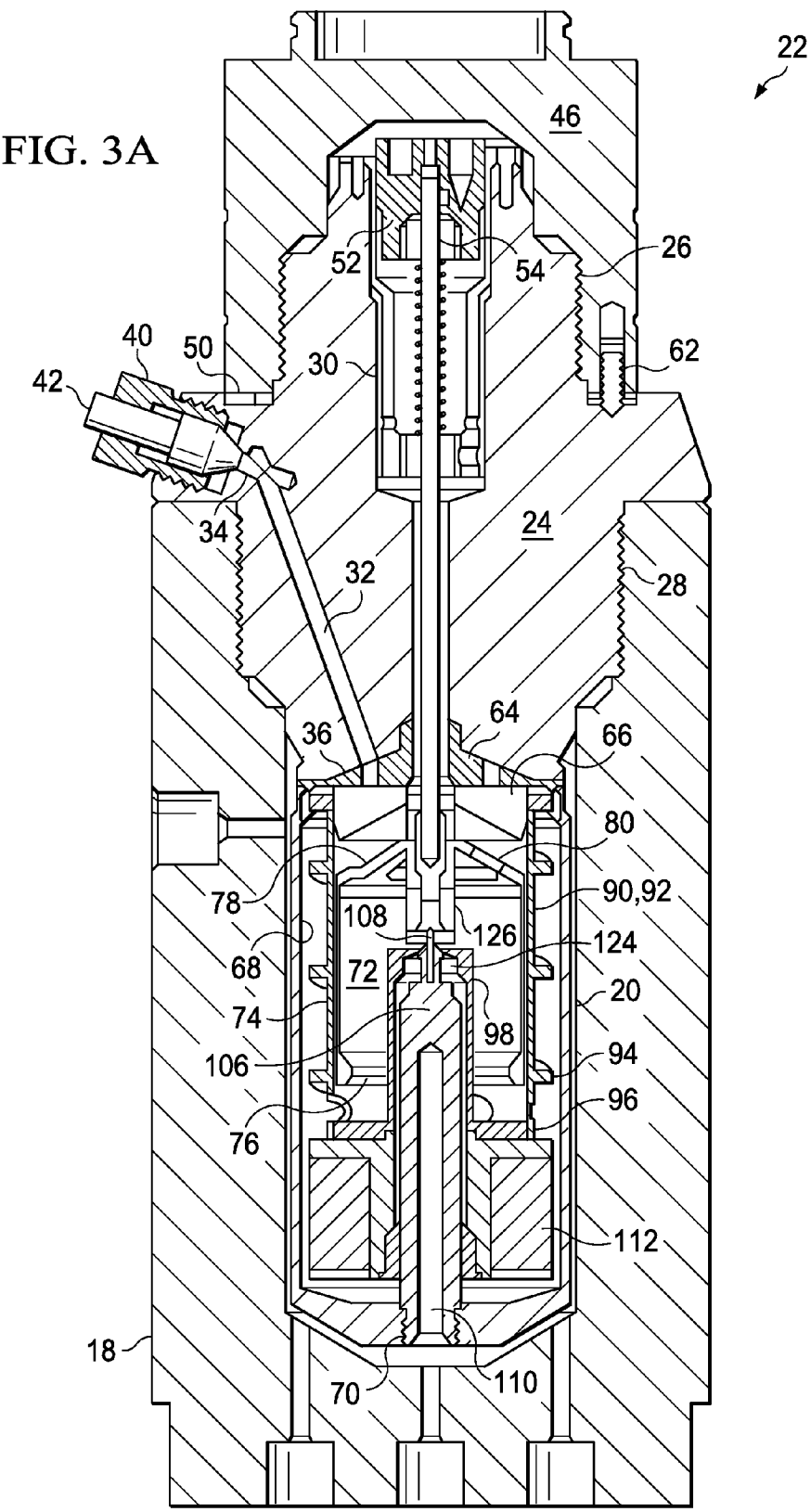
FIG. 3A provides a cross-sectional view of the plug and vessel assembly in FIG. 2.
Figure 3B:
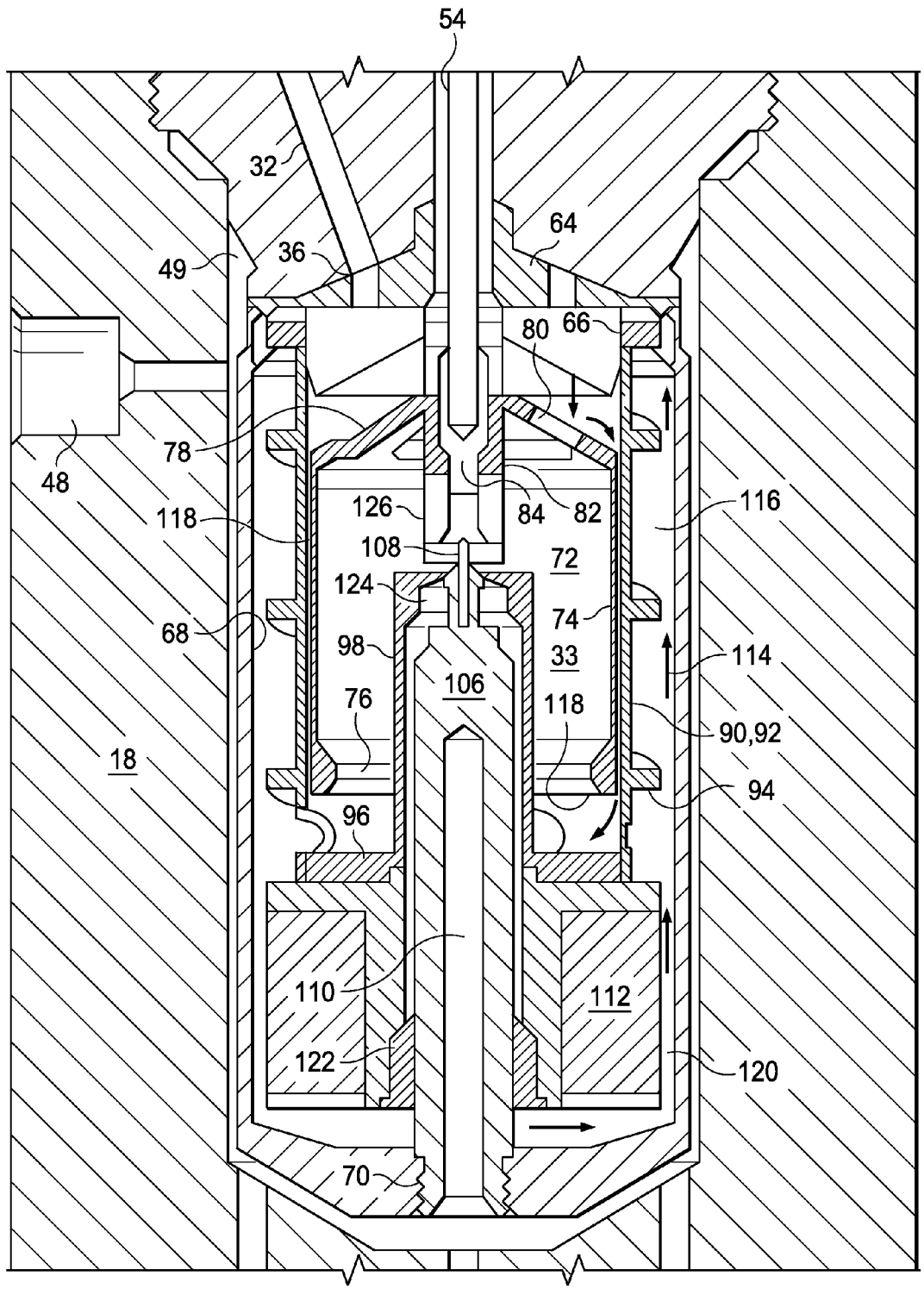
FIG. 3B provides an enlarged cross-sectional view of the plug and vessel assembly as shown in FIG. 3A.

Bob assembly 72 has a cylindrical outer body 74, a bottom surface 76, and a conical top surface 78 that defines a plurality of ports 80. Bob assembly 72 defines a downwardly extending cylindrical protrusion 82 (FIGS. 3A, 3B). Cylindrical protrusion 82 defines a receptacle 84 for receiving a lower end of shaft 54 of module assembly 52.

A rotor assembly 90 surrounds bob assembly 72. Rotor assembly 90 has a cylindrical body 92. Cylindrical body 92 has helical flutes 94 on an outside surface. Helical flutes 94 are provided to induce circulation of sample fluid as rotor assembly 90 is rotated. Rotor assembly 90 has a bottom surface 96 that extends upwardly to form an inner cylindrical protrusion 98. Inner cylindrical protrusion 98 supports radial bearing 124, which is supported by thermowell 106 and pivot 108. Bob assembly 72 is axially supported by pivot 108. Cavity 110 in thermowell 106 provides a space for centerline temperature measurement (FIG. 3B). Baffle assembly 64 is provided for eliminating or reducing angular momentum of sample fluid 33 induced by helical flutes 94. O-ring 102 (FIG. 4) and metal backup ring 104 surround plug 24 above pressure vessel 18.

Thermowell 106 (FIGS. 3A, 3B, 4) is threadably received in threaded orifice 70 of sample cup 68. Thermowell 106 has an upwardly extending pivot 108 that extends upwardly from an upper end. Thermowell 106 is received within inner cylindrical protrusion 98 of rotor assembly 90. Pivot 108 passes through a small orifice defined by an upper end of inner cylindrical protrusion 98 of rotor assembly 90. Inner magnetic drive 112 is located in sample cup 68 and surrounds thermowell 106. Inner magnetic drive 112 is affixed to a lower surface of rotor assembly 90 so that rotor assembly 90 is driven by the inner magnetic drive 112.

Circulation path 114 of sample fluid 33 includes annular volume 116 outside of rotor assembly 90, baffle assembly 64, and an annular volume 118 outside of bob assembly 72, ports 80 in conical top surface 78 of bob assembly 72, and a volume 120 surrounding inner magnetic drive 112. Second end 36 of sample filling passageway 32 communicates with annular volume 118.

Inner magnetic bushing 122 is located between thermowell 106 and inner magnetic drive 112. A rotor bearing 124 surrounds pivot 108 and is located within the inner cylindrical protrusion 98 of rotor assembly 90. A bearing 126 (e.g., a sapphire bearing) (FIG. 3B) is received within the downwardly extending cylindrical protrusion 82 of bob assembly 72. Bearing 126 engages an upper surface of the pivot 108 of thermowell 106. Bob assembly 72 is supported by bearing 126, which is supported on pivot 108 of thermowell 106.

Encoder assembly 128 (FIG. 1) is received on an upper surface of cap 46.

Plug assembly 22 may be removed from pressure vessel 18 after cooling the pressurizing fluid and sample and releasing pressure via hydraulic components 16.

Figure 7:
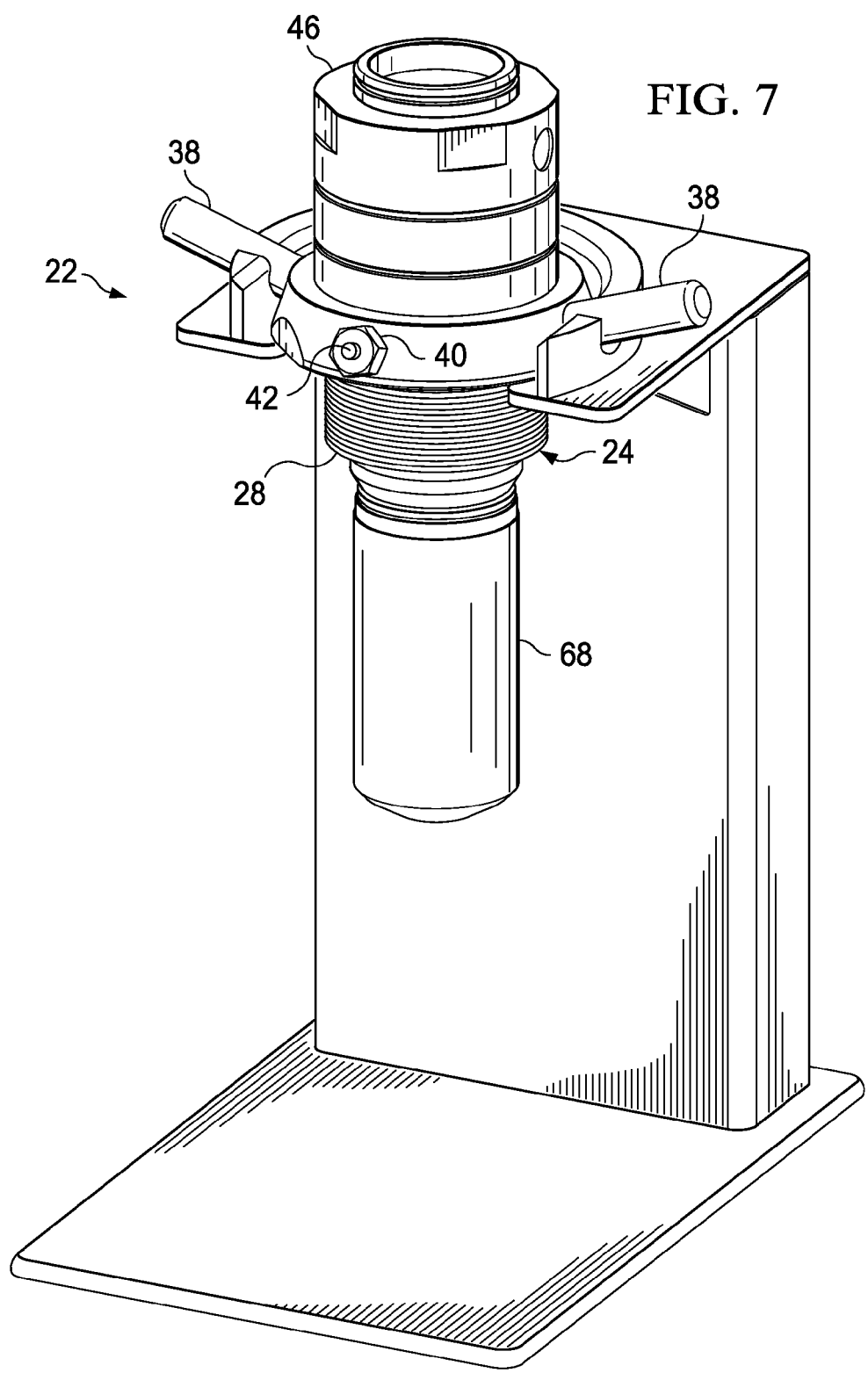
FIG. 7 provides a view of the plug assembly supported in the bench fixture.

In practice, sample fluid 33 is located in sample cup 68. Sample cup 68 is affixed to plug assembly 22. Plug assembly 22 is secured to pressure vessel 18, which locates sample cup 68 within receptacle 20 of pressure vessel 18. Sample fluid 33 is pressurized by application of pressure fluid 49 through hydraulic components 16. Sample fluid 33 and pressurizing fluids 49 are also heated using an external resistance heater surrounding pressure vessel 18. The viscosity of sample fluid 33 may then be measured once stable conditions of temperature and pressure are achieved. Once sample fluid 33 has been depressurized and cooled, plug assembly 22 may be removed with the attached sample cup 68. In a preferred embodiment, plug assembly 22 may be located in a stand as shown in FIG. 7 to facilitate removal of sample cup 68.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A viscometer comprising:
an instrument chassis;
a pressure vessel affixed to said instrument chassis, said pressure vessel defining a receptacle;
a plug assembly removably received within said receptacle of said pressure vessel, said plug assembly containing a spring and defining an orifice;
a sample cup in communication with said plug assembly;
a rotor assembly within said sample cup;
a bob within said rotor assembly;
a shaft passing through said orifice of said plug assembly, said shaft for communicating said bob and said spring;
wherein said sample cup is affixed to said plug assembly for removal with said plug assembly from said pressure vessel; and
wherein said pressure vessel remains affixed to said instrument chassis when said plug assembly is removed from said pressure vessel.

2. The viscometer according to claim 1 wherein:
an interior volume is defined by an inside of said sample cup;
an exterior volume is defined by an outside of said sample cup and an inside of said pressure vessel;
wherein said interior volume and said exterior volume are pressure balanced.

3. The viscometer according to claim 2 further comprising:
a rotor located within said interior volume of said sample cup;
a magnet located within said interior volume of said sample cup for driving said rotor.

4. A viscometer comprising:
a pressure vessel defining a receptacle;
a sample cup received in said pressure vessel, said sample cup defining an interior volume;
an exterior volume defined by an outside of said sample cup and an inside of said pressure vessel;
wherein said interior volume and said exterior volume are pressure balanced;
a plug assembly removably received within said receptacle of said pressure vessel, said plug assembly containing a spring and defining an orifice;
said sample cup affixed to said plug assembly;
a rotor assembly located within said sample cup;
a bob located within said rotor assembly;
a shaft passing through said orifice and communicating said spring and said bob;
wherein said sample cup and said attached plug assembly are removable as an assembly from said pressure vessel.

5. The viscometer according to claim 4 further comprising:
a rotor assembly located within said interior volume of said sample cup;
a magnet located within said interior volume of said sample cup for driving said rotor assembly.

6. A viscometer comprising:
a pressure vessel defining a receptacle;
a sample cup received in said receptacle of said pressure vessel, said sample cup defining an interior volume;
a magnet located within said interior volume of said sample cup;
a plug assembly removably received within said receptacle of said pressure vessel, said plug assembly containing a spring and defining an orifice;
a rotor assembly located within said sample cup;
a bob located within said rotor assembly;
wherein said plug assembly includes a plug top defining an orifice and a shaft passing through said orifice that communicates said spring and said bob;
said sample cup affixed to said plug assembly for removal with said plug assembly;
wherein said sample cup and said attached plug assembly are removable as an assembly from said pressure vessel.

7. The viscometer according to claim 6 further comprising:
a rotor assembly within said sample cup, said rotor assembly having helical flutes on an outer surface for inducing circulation of a sample fluid as said rotor assembly is rotated, said rotor assembly driven by said magnet.

8. The viscometer according to claim 6 further comprising:
said interior volume is defined by an inside of said sample cup;
an exterior volume is defined by an outside of said sample cup and an inside of said pressure vessel;
wherein said interior volume and said exterior volume are pressure balanced.

9. A method operating a viscometer comprising:
locating a sample fluid in a sample cup having an open end;
affixing said open end of said sample cup to a plug assembly to form an assembly, said plug assembly containing a spring and defining an orifice;
locating said sample cup in a pressure vessel;
locating a rotor assembly within said sample cup;
locating a bob within said rotor assembly;
rotating said rotor assembly;
passing a shaft through said orifice for communicating said spring and said bob;
heating and pressurizing said sample fluid;
measuring an angular displacement of said spring for measuring a viscosity of said sample fluid;
cooling and depressurizing said sample fluid;
removing said plug assembly containing said spring and removing said affixed sample cup from said pressure vessel as said assembly.

10. The method according to claim 9 further comprising the step of:
locating said plug assembly and said sample cup in a stand for providing easy access to said sample cup.

11. A viscometer comprising:
a pressure vessel defining a receptacle;
a plug assembly removably received within said receptacle of said pressure vessel, said plug assembly including a plug top, said plug top defining an orifice and containing a spring;

a sample cup having an open end, said open end attached to said plug assembly;

a rotor assembly located within said sample cup;

a bob located within said rotor assembly;

a shaft passing through said orifice of said plug top, said shaft communicating said spring and said bob;

wherein said sample cup and said attached plug assembly are removable as an assembly from said pressure vessel.

* * * * *